United States Patent [19]
Ritter et al.

[11] Patent Number: 6,128,174
[45] Date of Patent: Oct. 3, 2000

[54] METHOD AND APPARATUS FOR RAPIDLY CHANGING A MAGNETIC FIELD PRODUCED BY ELECTROMAGNETS

[75] Inventors: Rogers C. Ritter, Charlottesville, Va.;
Peter R. Werp, Los Gatos, Calif.;
Michael A. Lawson, Ballwin, Mo.

[73] Assignee: Stereotaxis, Inc., St. Louis, Mo.

[21] Appl. No.: 08/921,298

[22] Filed: Aug. 29, 1997

[51] Int. Cl.$^7$ ...................................................... H02N 15/00
[52] U.S. Cl. ............................................ 361/143; 361/141
[58] Field of Search ..................................... 361/143, 141, 361/152–156, 160, 170, 144

[56] References Cited

U.S. PATENT DOCUMENTS

| | | | |
|---|---|---|---|
| 3,358,676 | 12/1967 | Frei et al. | 128/1.3 |
| 3,674,014 | 7/1972 | Tillander | 128/2.05 R |
| 3,941,119 | 3/1976 | Corrales | 128/2 M |
| 4,869,247 | 9/1989 | Howard, III et al. | 128/303.1 |
| 5,125,888 | 6/1992 | Howard et al. | 600/12 |
| 5,332,987 | 7/1994 | Hennessy et al. | 335/216 |
| 5,334,207 | 8/1994 | Gay, Jr. | 606/7 |
| 5,353,807 | 10/1994 | DeMarco | 128/772 |
| 5,558,091 | 9/1996 | Acker et al. | 128/653.1 |
| 5,600,245 | 2/1997 | Yammamoto et al. | . |
| 5,602,711 | 2/1997 | Curtis et al. | 361/144 |
| 5,654,864 | 8/1997 | Ritter et al. | 361/141 |
| 5,677,821 | 10/1997 | Myr | 3691/144 |

FOREIGN PATENT DOCUMENTS

| | | | |
|---|---|---|---|
| WO 96/037955 | 2/1996 | WIPO | H02N 15/00 |

OTHER PUBLICATIONS

"Characteristics of an Improved Magnetic–Implant Guidance System," Robert G. McNeil et al., IEEE Trans. Biomed. Eng., vol. 42, No. 8, Aug. 1995, pp. 802–808.

"Functional Design Features and Initial Performance Characteristics of a Magnetic–Implant Guidance System for Stereotactic Neurosurgery," Robert G. McNeil et al., IEEE Trans. Biomed. Eng., vol. 42, No. 8, Aug. 1995, pp. 793–801.

"Magnetic Manipulation Instrumentation for Medical Physics Research," G.T. Gillies et al, Rev.Sci.Instrum., (65)3:533–562 (1994) No Month Provided.

"Goniometric Motion Controller for the Superconducting Coil in a Magnetic Stereotaxis System," Elizabeth G. Quate et al., IEEE Trans. Biomed. Eng., vol. 38, No. 9, Sep. 1991, pp. 899–905.

(List continued on next page.)

*Primary Examiner*—Fritz Fleming
*Attorney, Agent, or Firm*—Doepken Keevican & Weiss

[57] ABSTRACT

A method and apparatus for ramping current in an electromagnet in which a coil is used to generate the magnetic field provides rapid changes in the generated magnetic field. The method allows a change in current in the coil to be accomplished more rapidly than by applying a step change in voltage, when superconducting coils subject to quenching are used or when nonsuperconducting coils subject to other physical limitations are used. The method requires that both the current $I(t)$ through the coil and the first derivative of the current vary with respect to time t during the ramping period, so that magnitude of the derivative of the current is higher when the magnitude of applied current is lower, lower when the magnitude of the applied current is higher. One variation of this method supplies (or removes) a constant amount of power from the magnetic field of the magnet, while another variation compensates for both self-generated eddy current losses and self-generated high field effects. The method can be used to guide a magnetic seed and in other applications. The apparatus includes, in its most general form, an electromagnetic coil, a generator for applying an initial current to the coil, and a processor controlling the generator that causes the current to ramp from an initial to a final value in accordance with the methods described above.

49 Claims, 5 Drawing Sheets

OTHER PUBLICATIONS

"Nonlinear magnetic stereotaxis: Three–dimensional, in vivo remote magnetic manipulation of a small object in canine brain," M.S. Grady et al., Med. Phys. 17(3), May/Jun. 1990, pp. 405–415.

"A New Magnet System for 'Intravascular Navigation', " Shyam B. Yodh, et al., Med and Biol. Engrg. (6):143–147 (1968) No Month Provided.

"Symposium on BioEngineering: Magnetic Forces for Medical Applications," D. Bruce Montgomery and R. J. Weggel, Journal of Applied Physics 40:1039–1041, (1969). No Month Provided.

"Superconducting Magnet System for Intravascular Navigation," D. B. Montgomery et al, Journal of Applied Physics 40:2129–2132 (1969). No Month Provided.

"The Design of a 2T Superconducting Solenoid for Magnetic Catheter Guidance," J.R. Hale, et al. IEEE Transactions on Magnetics, (MAG–11)2:563–564 (1975) No Month Provided.

"Medical Applications of Magnet Devices," J.R. Hale, IEEE Transactions on Magnetics, (Mag–11) 5:1405–1407 (1974) No Month Provided.

"Magnetically Controlled Intravascular Catheter," John Alksne, Surgery, (61)1:339–345 (1968).

"Ferromagnetic Embolization," Jane Barry et al, Radiology, (138):341–349 (1981).

"The Pod and its Applications," E.H. Frei et al, Med. Res. Eng., (5)4:11–18 (1966).

"Development and Use of the POD Catheter in the Cerebral Vascular System," J. Driller et al, Med. Res.Engrg, (8):11–16 (1969).

"Selective Cerebral Catheterization," Johnathan Molcho et al, IEEE Transactions on Bio–Medical Engineering, (BME–17)2:134–140 (1970).

"Selective Angiography with a Catheter Guided by a Magnet," H. Tillander, IEEE Transactions on Magnetics, (Mag–6)2:355–358 (1970).

"Kinetics of Magnetically Guided Catheters," Jack Driller, IEEE Transactions on Magnetics, (Mag–6)2:467–471 (1970).

"Magnetic Materials as Biological Implants—Criteria for Selection," Jack Driller and Victor Parsonnet, IEEE Trans. on Magnetics, (Mag–9)3:444–447 (1973).

"Design Aids for Simple Magnet Systems Useful in Biomedical Applications," Jack Driller and Bruce Sollish, IEEE Trans. on Biomedical Engineering, (BME–20)6:459–464 (1973).

"Magnetically Guided Devices for Vascular Exploration and Treatment," Sadek K. Hilal et al, Radiology, (113):529–540 (1974).

"A Rotating D.C. Superconducting Magnet System for Guidance of Intravascular Catheters," S.R. Savitz et al, in Proc. of 28th Ann Conf on Engineering and Biology, (17):422 (1975).

"Magnetics for Power and Control of Body Implants," George D. Summers, in Proc of Fifth National Biomedical Sciences Instrumentation Symposium, (4):293–302 (1967).

"A Flying Superconducting Magnet and Cryostat for Magnetic Suspension of Wind–Tunnel Models," C. Britcher et al, Cryogenics, 185–189 (1984) (p. 188 not available).

"Off–Axis Helmoltz Field," J. Higbie, Am J. Phys. (46)10:1075–1076 (1978).

"Maximum Current in a Superconducting Wire," E. Yu. Klimenko et al, Sov. Phys. Dokl (30)6: 518–520 (1985).

"Magnetic Guidance of a Catheter with Articulated Steel Tip," Hans Tillander, Acta Radiologica, (35):62–64 (1951).

"External Magnetic Guidance of Endovascular Catheters with a Superconducting Magnet: Preliminary Trials," A. Gaston et al, J. Neuroradiol., (15):137–147 (1988).

"A Review Of Medical Applications Of Magnet Attraction And Detection," Driller et al., (11)6:271–277 (1987).

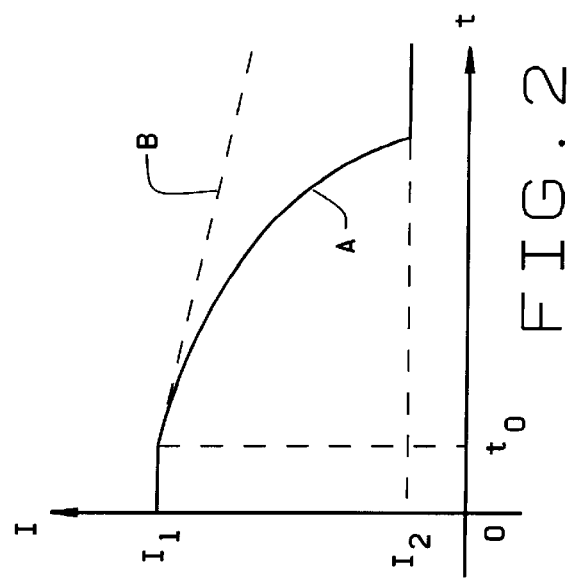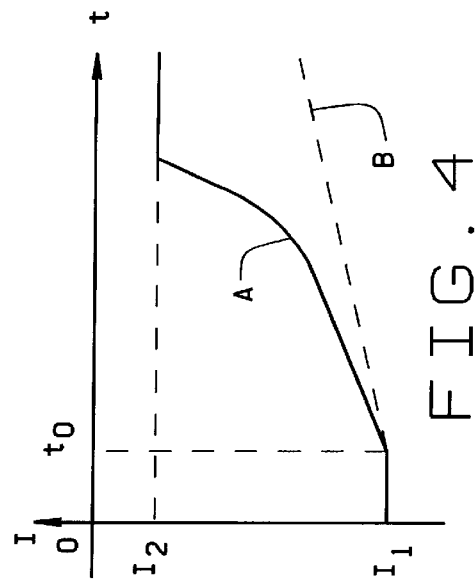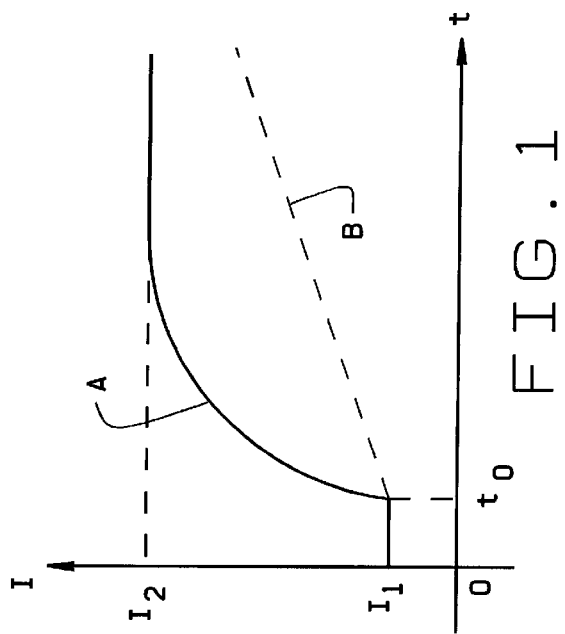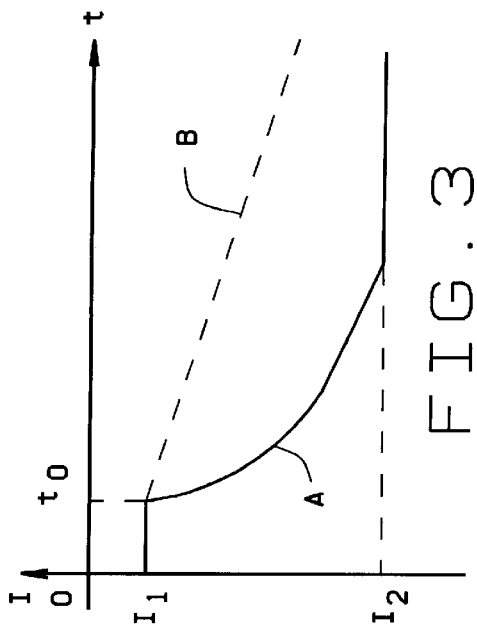

METHOD AND APPARATUS FOR RAPIDLY CHANGING A MAGNETIC FIELD PRODUCED BY ELECTROMAGNETS

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

This invention relates to a method of controlling electromagnets, and more specifically to a method of controlling current changes in, and thus magnetic fields produced by, electromagnets by using a patterned rate of current change in a manner to cause the electromagnets to function faster, more efficiently, more safely, or more economically, or in a manner in which a combination of these advantages accrue.

2. Description of Related Art

Electromagnets of various types have been used for such diverse purposes as the magnetic suspension of wind-tunnel models and the guiding of implant placement in living tissue to deliver therapy to a patient. In these and in many other applications, it has proven useful to control the power source of the electromagnet with feedback systems having characteristics designed to satisfy load requirements or system requirements, or both. Often, it would be advantageous to allow these power sources to provide rapid current changes in response to conditions imposed by or on the system that is influenced by the magnetic field of the electromagnet.

Superconducting magnets made of coils of superconducting material (especially the new, high-temperature type of superconductors) present special problems when rapid current change is required. Superconducting coils have zero resistance, except for parasitic resistance that includes their external leads and connections to the powering device. Therefore, these coils have a long time constant for the increase of current, given by the value of L/R, where L is coil inductance and R is the effective value of the various sources of parasitic resistance. Because R is very low, superconducting coils act as almost pure inductors, and have very long time constants.

In a typical prior art use of superconducting magnets (such as described in McNeil et al., "Characteristics of an Improved Magnet-Implant Guidance System," pp. 802–808, IEEE Trans. Biomed. Eng., Vol. 42, No. 8, August 1995, which is hereby incorporated by reference in its entirety), a constant voltage V is applied to the superconducting coil. Thus, a good approximation of the ramping rate of current through the coil is given by assuming the coil acts as a pure inductance, i.e., dI/dt=V/L. Unless the applied voltage V is very large, or L is very small, the rate of current increase is low. Large coils can thus require hours, or even days, to power up, which is at least inconvenient and may be intolerable in some applications. Attempts to increase the ramping rate by using moderately high values of constant voltage V can result in quenching (i.e., loss of conductivity) of the superconducting coil, which can be hazardous to equipment. In addition, a high voltage could be established in the coil in some transient circumstances, possibly exceeding the breakdown voltage of the coolant (such as helium, or helium gas bubbles, which may also be present) and causing serious coil damage.

Coils can quench as a result of a combination of two factors: (a) an excessively high magnetic field resulting from excessive current in the coil, and (b) eddy-current heating resulting from current changes being applied to the coil too rapidly. (High fields and eddy current heating can result either from current in the coil itself, or from nearby sources of magnetic fields. The effect of nearby sources of magnetic fields is not hereafter explicitly taken into account, because these effects are of secondary significance in most applications. There are also other factors that are difficult to model mathematically that are known to contribute to the tendency of a coil to quench—e.g., liquid helium proximity to the coil, and the thermal capacity and conductivity of the coil bobbin and support structure. Thus, the quenching behavior of any particular coil can usually only be determined by experimentation and modeled approximately.) It is well-known that a given superconducting coil will quench at a lower current if the ramping rate (i.e., first derivative of the current) is high, and also that it will quench at some lower ramping rate if the field (i.e., the current itself) is high. Taken together, these effects combine so that there is a tendency for quenching to occur at a roughly constant value of the magnitude of the product of the current and its rate of change (i.e., the first derivative of the current). It would be desirable to provide a faster method of ramping current in superconducting coils that avoids the problem of quenching.

It would also be desirable if a high voltage magnitude, when used to ramp the coil, could be maintained only up to the arcing limit of the coil while the magnitude of current in the coil is low, and a lower magnitude of voltage applied as the magnitude of current increases. Such a method would allow rapid ramping of current while avoiding the risk of damage caused by insulator breakdown.

The limitations of superconducting coils when used with most present current ramping methods are so severe as to prevent the use of such coils in traditional servo systems or in manners in which limited ramp time is important. In other applications, designers have been forced to limit the rate of change of current to a value found to avoid quenching in worst case conditions, and to limit the current itself to a value found to avoid quenching. Alternately, if faster ramping is needed, coil designers have had to undertake heroic steps to make the coil less vulnerable to ramp-time quench, although these steps can never completely avoid the possibility of quench. Consequently, the use of superconducting coils in dynamic devices has been almost completely ruled out.

More specifically, the temperature T and field $H_c$ at which a superconducting wire will change phase is given approximately by the equation $$H_c = H_o[1-(T/T_c)^2] \quad (1)$$

for an especially simple superconducting material, and by modified versions of the equation for others. Here, $H_c$ is the critical field above which the material will change phase, $H_o$ is the critical field at absolute zero temperature, and $T_c$ is the critical temperature above which the material will not be superconducting at any field value. Thus, the tendency of a coil to quench will depend on its own current (an I-dependence), in addition to fields created by external sources. In summary, coils can quench from high field effects or eddy-current heating from ramping too fast. The high field effects or eddy-current heating can be caused by the coil itself, or by other nearby sources.

As described above, power supplies of fixed voltage have been used in the prior art to provide linear ramping of a single superconducting coil. Standard servo methods have been used for ramping non-superconducting coils. In the less common case of multi-coil systems, special temporal relationships have been used in more complex ramping systems, such as in allowed U.S. patent application Ser. No. 08/280,124, filed Jul. 25, 1994, and in currently pending U.S. patent application Ser. No. 08/682,867, filed Jul. 8, 1996. The specifications of both of these patent applications are incorporated herein in their entirety. In one use of superconducting electromagnets, a six-coil helmet (such as described in McNeil et al., "Functional Design Features and Initial Performance Characteristics of a Magnetic-Implant Guidance System for Stereotactic Neurosurgery," pp. 793–801, IEEE Trans. Biomed. Eng., Vol. 42, No. 8, August 1995 which is hereby incorporated by reference in its entirety) was designed to move a magnetic implant object ("seed") around within a human brain (or some other part of a human body) to deliver therapies such as selective hyperthermia, radioactivity, chemicals, or other substances.

A control method described in McNeil et al., "Characteristics of an Improved Magnetic-Implant Guidance System," pp. 802–808, IEEE Trans. Biomed, Eng., Vol. 42, No. 8, August 1995 (which is hereby incorporated by reference in its entirety) partially avoided the usual limitations encountered in ramping a superconducting coil by controlling coils in pairs in which the two members of each coil pair operate in a different dynamic manner to provide stepwise, impulsive forces on the seed. The current through a main, pulling coil is kept at a subthreshold level (i.e., below a value required to move a seed in a brain, in the disclosed application) throughout each step. Current in a much closer partner coil (a "boost" or "push-pull" coil) is then ramped up a small amount to apply an opposite field by additive gradient (of magnetic field) on the seed. Because it is closer to the seed, the gradient caused by the closer coil can be much greater without reversing the seed direction, so a large pushing impulsive force could be applied. The push-pull coil then has its gradient reversed to pull, for a short time, against the main pulling coil to halt the seed movement and reestablish a stable position at rest. The gradient of the push-pull coil falls off rapidly with distance from the coil, approximately as the fourth power of the distance. Therefore, the close coil can effect great changes in force at the seed position with small changes in a small current. Modifications to this technique can be used in cases in which the main, pulling coil is not at a much greater distance from the seed than the partner coil. This technique and its modifications can be accomplished with constant voltage ramping in accordance with the prior art, but limitations inherent in constant voltage ramping considerably restrict the speed of the motion of the seed. These limitations come about because the maximum voltage magnitude that can be applied can be no greater than that which results in quenching when applied simultaneously with the maximum allowable current in the coil. By restricting the maximum voltage magnitude, the rate at which coil current changes can be accomplished, and hence the rate at which changes in the resulting magnetic field can be made that effect movement of the seed, is limited.

It would therefore be advantageous if a ramping method were available for coils that could minimize ramping time between two current levels, while avoiding quenching and arcing. It would be particularly advantageous if this system were applicable to systems employing multiple coils to apply force and/or direction to a magnetic seed.

SUMMARY OF THE INVENTION

One embodiment of the invention is a method of rapidly changing a magnetic field produced by an electromagnetic coil (usually, but not necessarily, a coil having a winding comprising a superconducting material, herein referred to as a superconducting coil or magnet) comprising the steps of (a) applying a first current $I_1$ (which may be zero current) to the coil, (b) transitioning to a second current $I_2$ (which may be zero, but which is different from $I_1$ in that it has a magnitude or direction, or both, different from $I_1$; i.e., $I_1 \neq I_2$) applied to the electromagnetic coil, and (c) during a transition period between the application of $I_1$ and $I_2$, changing the current applied to the coil in a manner in which, during at least a portion of the transition period, the first derivative of the current varies, so that the coil is ramped from $I_1$ to $I_2$ more rapidly than would be the case with constant voltage ramping, which produces a current having a constant first derivative. This is achieved by controlling the time-varying current during the transition period so that the magnitude of $dI(t)/dt$ varies in a direction opposite to that in which the magnitude of (t) varies; i.e., when I(t) is large, $dI(t)/dt$ is small, and vice versa. More preferably, during at least a portion of the transition period, $d^2I(t)/dt^2$ has a sign opposite to that of $I_1$ when I(t) has the same sign as $I_1$, and $d^2Id(t)/dt^2$ has a sign opposite to that of $I_2$ when I(t) has the same sign as $I_2$. Also, the sign of $dI(t)/dt$ is the same as the sign of the quantity $(I_2-I_1)$, and the magnitude of the first derivative of I(t) is, during the transition period, at least sometimes greater than $|V_{max}|/L$, and preferably (but not necessarily) never less than $|V_{max}|/L$, and even more preferably, always greater than $|V_{max}|/L$.

The invention is sufficiently general to encompass ramping methods in which initial and final currents may have arbitrary signs. The complexity of the explanation of the invention is necessarily increased to encompass the generality of the invention. However, the inventive methods do not require the initial and final currents to have arbitrary signs. It will be recognized by those skilled in the art upon studying the description of these methods that the methods can be practiced in any ramping application, irrespective of any other constraints placed on the initial and final currents. Thus, the inventive methods can be applied, for example, to applications that require coil currents to vary only between zero and some positive value (i.e., current flow in the coil is only in one direction).

The restriction on the sign of the second derivative need not apply during the entire transition period between $I_1$ and $I_2$, because a rapid "head start" or "leap forward" can occur with this method of ramping, as will be described in the detailed explanation that follows.

As an example of the inventive ramping method, let us assume that a small, positive (or zero) constant current $I_1$ is first applied to the coil, and that the desired final current is $I_2$, a larger positive current. The second derivative of I(t) (i.e., $d^2I(t)/dt^2$) is negative during at least a portion of the transition from $I_1$ to $I_2$, in accordance with the invention. Also, between the application of current $I_1$ and the subsequent application of the larger, positive current $I_2$, current in the coil first undergoes a relatively rapid change. As the current in the coil approaches $I_2$, the magnitude of the rate of change decreases. When $I_2$ is reached, the current is again held constant. It will be recognized that the first derivative of the coil current need not be, and generally will not be continuous at the moment the coil current is increased from $I_1$, and it should be understood that it also need not be continuous at the moment the coil current reaches $I_2$, i.e., when the ramping stops.

Other embodiments of the invention provide ramping in accordance with the more general embodiment described above, but with more specific ramping conditions that meet various constraints selected to approach a maximum safe ramping rate while minimizing risk of producing quenching conditions in a superconducting coil. For example, in accordance with one variation of the invention, a changing amount of current is supplied to a coil in a manner that maintains a constant flow of power into (or out of) the magnetic field of the magnet. (For notational convenience, a flow of power "into" the magnetic field, unless otherwise noted, should hereafter be construed, for description convenience, as encompassing a flow "out of" the field, as well.) A second variation more optimally minimizes heat losses within the electromagnet that may otherwise cause it to quench, while at the same time minimizes the time required to change the current in the magnet by a given amount. This second variation also advantageously compensates for both self-generated eddy current losses and self-generated high field effects. Other variations are also provided that more closely take into account empirically observed limitations of particular superconducting or non-superconducting coils.

Another embodiment of the invention comprises, in its most general form, a device for rapidly changing a magnetic field having a controlled magnitude, in which the device comprises (a) an electromagnetic, preferably superconducting, coil; (b) means for applying a first current of $I_1$, Amperes to the coil; (c) means for transitioning to a second current of $I_2$ Amperes applied to the coil; and (d) means for applying a time-varying current I(t) to the coil between application of $I_1$ to the coil and application of $I_2$ to the coil, where dI(t)/dt varies as a function of time t, and the magnitude of dI(t)/dt varies in a direction opposite to that in which the magnitude of I(t) varies.

It is thus an object of the invention to provide a method of ramping current in a coil and thus change its magnetic field more rapidly than the prior art constant voltage method.

It is another object of the invention to provide a rapid current ramping method for a superconducting coil that avoids arcing and quenching of the coil.

It is yet another object of the invention to provide a current ramping method that can be used to rapidly guide a seed with a system of multiple electromagnetic coils, especially when the coils are superconducting coils.

It is still another object of the invention to provide an apparatus for rapidly ramping current in electromagnetic coils.

These and other objects of the invention will become evident to those skilled in the art upon review of the detailed description of the invention and the accompanying figures.

BRIEF DESCRIPTION OF THE DRAWINGS

FIG. 1 is a graph comparing constant-voltage and constant-power current ramping in an electromagnetic coil from a small magnitude positive current to a larger magnitude positive current;

FIG. 2 is a graph comparing constant-voltage and constant-power current ramping in an electromagnetic coil from a large magnitude positive current to a smaller magnitude positive current;

FIG. 3 is a graph comparing constant-voltage and constant-power current ramping in an electromagnetic coil from a small magnitude negative current to a larger magnitude negative current;

FIG. 4 is a graph comparing constant-voltage and constant-power current ramping in an electromagnetic coil from a large magnitude negative current to a smaller magnitude negative current;

FIGS. 1–6 and 10 are intended to provide only indications of relative magnitudes, slopes and directions rather than precise numerical values of the indicated quantities, and are therefore drawn to an arbitrary scale.

DESCRIPTION OF THE PREFERRED EMBODIMENTS

Figure 6:
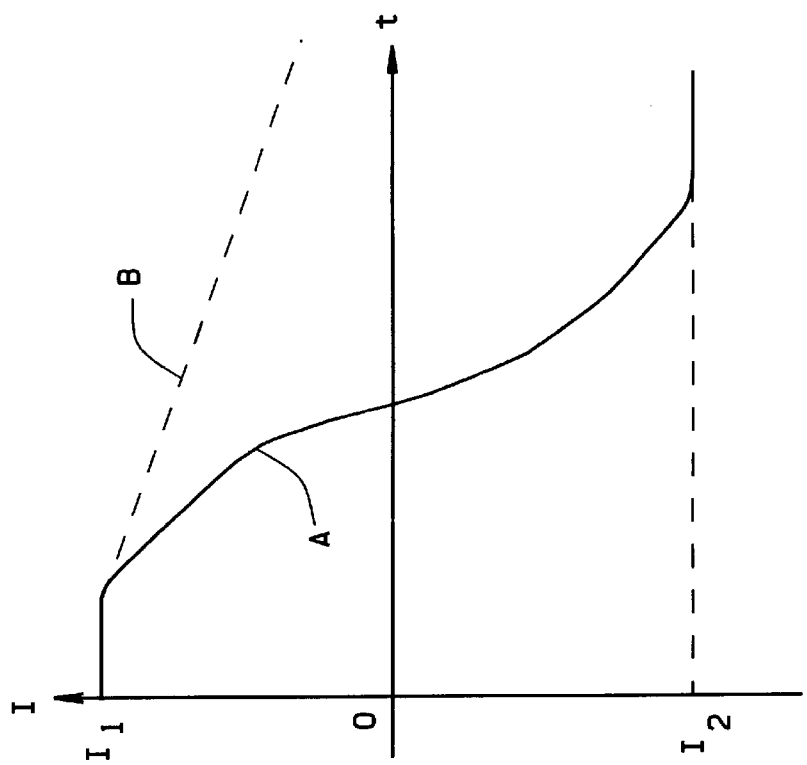
FIG. 6 is a graph comparing constant-voltage and constant-power current ramping in an electromagnetic coil from a positive current to a negative current.

In accordance with the invention, quenching of a superconducting coil is avoided by controlling the amount of current I through the coil, its rate of change dI/dt, and the second derivative of the current $d^2I/dt^2$, during a period of transition from one current level to another. In one embodiment of the invention, during the transition period between the application of a first coil current $1_1$ (which may be zero current) and a second coil current $I_2$, the current applied to the coil is changed (i.e., "ramped") in a manner in which, during a transition period between the application of $I_1$ and $I_2$, changing the current applied to the coil in a manner in which, during at least a portion of the transition period:

i) if $I_1$ and $I_2$ are both positive, the second derivative of I(t) is negative;
ii) if $I_1$ and $I_2$ are both negative, the second derivative of I(t) is positive;
iii) $I_1$ is negative and $I_2$ is positive, the second derivative of I(t) is positive until I(t) itself reaches zero, following which the second derivative of I(t) is negative;
iv) $I_1$ is positive and $I_2$ is negative, the second derivative of I(t) is negative until I(t) itself reaches zero, following which the second derivative of (t) is positive;

in addition to which:

v) if $I_2$ is greater than $I_1$, the first derivative of I(t) is positive;
vi) if $I_1$ is greater than $I_2$, the first derivative of d(t) is negative;

and also in addition to which:

vii) the magnitude of the first derivative of I(t) is, during the transition period, not less than, and at least sometimes greater than $|V_{max}|/L$;

where I(t) is the current as a function of time t during the transition period, $|V_{max}|$ is a maximum voltage magnitude that can be applied to the coil at a current $|I_{max}|$ without quenching if the coil is a superconducting coil (where $I_{max}$ may be a rated maximum current of the coil), L is the inductance of the coil, and $|I_{max}|$ at least equal to the greater of $|I_1|$ and $|I_2|$, so that the change from $I_1$ to $I_2$ is accomplished more rapidly than would occur if a constant voltage limited to be within a range that does not cause the coil to quench when the constant voltage is applied at the coil's maximum rated current were applied to the coil to produce the same current change.

The restriction on the sign of the second derivative need not apply during the entire transition period between $I_1$ and $I_2$, because a rapid "head start" or "leap forward" can occur with this method of ramping, as will be described below.

Ensuring that the above conditions are met allows the average value of dI/dt to be greater in magnitude during the transition than would otherwise be possible without quenching superconducting coils if the transition were controlled by stepping a voltage source between two voltages, in accordance with a prior art method of ramping coils. This advantage accrues because the power that goes into raising the coil temperature is a smaller fraction of the power that is being put into (or taken out of) the magnetic field than is the case with prior art methods. Furthermore, as can be seen from the relationship of dI/dt to voltage, a high voltage magnitude need only be applied to the coil while the current magnitude is low, and a lower voltage magnitude is applied as the current magnitude increases, avoiding the risk of damage caused by insulation breakdown.

It should be noted that the inventive techniques are equally applicable to both superconducting and nonsuperconducting coils. In the case of a nonsuperconducting coil that is not subject to quenching, the same inventive methods disclosed herein may be used to maintain and/or control other operating characteristics of the coil. By way of example only, and not to limit the invention in any way, the inventive methods may be used to prevent undesirable overheating of a nonsuperconducting coil, or to avoid operating modes that might cause insulation breakdown or make such breakdown more likely to occur. Typically, quenching limits described herein are interchangeable with many non-superconducting coil limitations for purposes of this invention. For example, the limits on $|V_{max}|$ and $|I_{max}|$ for a nonsuperconducting coil may be set at levels that avoid overheating of the coil, or arcing.

In another variation of the inventive method, an increasing amount of current is supplied to a coil in a manner that maintains a constant flow of power into (or out of) the magnetic field of the magnet. To accomplish this, current is controlled so that it rises proportionately to the square root of elapsed time (assuming that the initial current is zero). This method, which we call the "constant power ramp" or more simply the "constant power" method, is particularly amenable to systems having multiple coils and requiring complex synchronization of the fields of the coils.

According to the constant power ramp method, a time-varying current I(t) is applied to an electromagnet coil, the magnitude of the current varying in accordance with the expression $$I^2(t)=I_o^2+(2P_o/L)(t-t_o),\qquad(2)$$

where $I_o$ is the current at a starting time $t_o$, $P_o$ is a selected constant value of power (which may be determined in accordance with a procedure described below), and L is the self-inductance of the electromagnet. If $I_o$ is zero at time $t_o$, then the magnitude of the time-varying current applied to the coil increases as the square root of elapsed time until it reaches a desired value (which may be a required value dictated by the application), and then it is kept constant until another change is desired.

Those skilled in the art will observe that eq. 2 implicitly requires taking square roots to solve for I(t):

$$I(t)=\pm[I_o^2+(2P_o/L)(t-t_o)]^{1/2}.\qquad(3)$$

(Note that $P_o$ is taken as positive when power is being delivered to the coil, and negative when power is being extracted from the coil.) In each of FIGS. 1 to 6, curve A represents a qualitative graph of current vs. time for the constant-power ramping method. Also shown in each of these figures, for comparison purposes, is a curve B (actually, a straight line) showing current vs. time for constant-voltage ramping.

FIG. 1 is a graph of coil current vs. time for a case in which both the starting current $I_1$ and the final current $I_2$ are positive values, and $I_2>I_1$. In this case, $P_o$ is positive, because power is being supplied to the coil. It can also be seen that the second derivative of the current with respect to time is negative, i.e., the rate of change of current decreases with respect to time.

FIG. 2 is a graph of coil current vs. time for a case in which both the starting current $I_1$ and the final current $I_2$ are positive values, and $I_2<I_1$. In this case, power is being extracted from the coil, so $P_o$ is taken to be negative. The second derivative of the current is also negative in this case, although the magnitude of the current change increases with respect to time.

FIG. 3 is a graph of coil current vs. time for a case in which both the starting current $I_1$ and the final current $I_2$ are negative values, and $|I_2|>|I_1|$. In this case, $P_o$ is positive, because power is being delivered to the coil. The second derivative of the current is positive in this case, because the rate at which the current becomes increasingly negative decreases with increasing time.

FIG. 4 is a graph of coil current vs. time for a case in which both the starting current $I_1$ and the final current $I_2$ are negative values, and $I_2>I_1$. In this case, power is being extracted from the coil, so $P_o$ is taken to be negative. The second derivative of the current is positive in this case, because the rate at which the current becomes increasingly negative decreases with increasing time.

Figure 5:
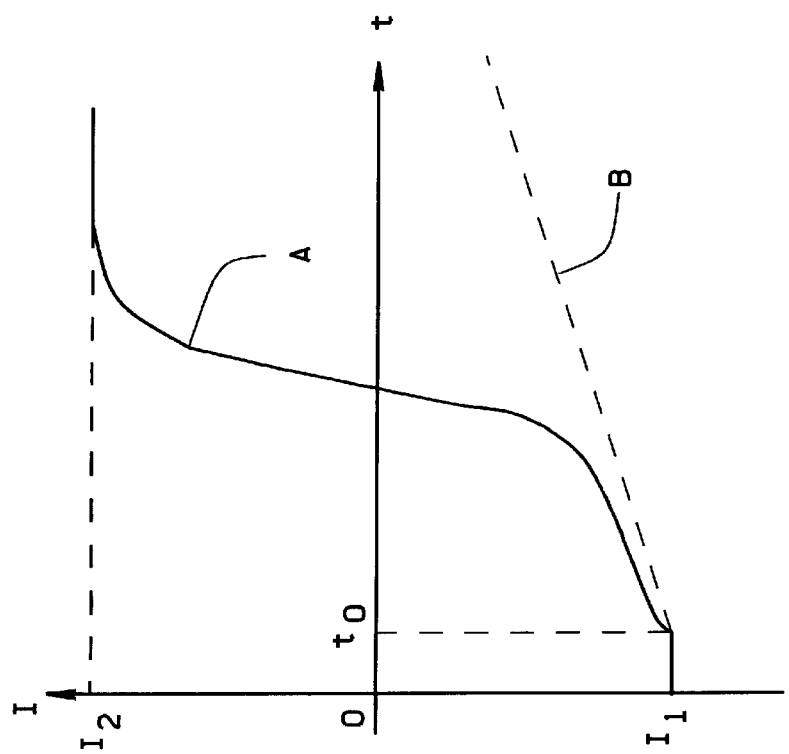
FIG. 5 is a graph comparing constant-voltage and constant-power current ramping in an electromagnetic coil from a negative current to a positive current.

FIG. 5 is a graph of coil current vs. time for a case in which the starting current $I_1$ is negative and the final current $I_2$ is positive. In this case, power is initially extracted from the coil until zero current is reached, and then power is applied to the coil. For this reason, $P_o$ is taken to be negative while the current in the coil is negative, and positive while the current in the coil is positive. Until the current reaches zero, this case is identical to that of FIG. 4. After the current reaches zero, this case is identical to that of FIG. 1.

FIG. 6 is a graph of coil current vs. time for a case in which the starting current $I_1$ is positive and the final current $I_2$ is negative. In this case, power is initially extracted from the coil until zero current is reached, and then power is applied to the coil. For this reason, $P_o$ is taken to be negative while the current in the coil is positive, and positive while the current in the coil is negative. Until the current reaches zero, this case is identical to that of FIG. 2. After the current reaches zero, this case is identical to that of FIG. 3.

FIGS. 1–6 show $d^2I/dt^2$ having the same sign for the entire period between application of current $I_1$ and $I_2$ (at least until I(t) itself changes sign or passes through zero). In accordance with the invention, it is required that this relationship hold for at least a portion of this period sufficient to cause the current to change from $I_1$ to $I_2$ in less time than would otherwise be necessary for ramping to occur using a constant applied voltage limited to a range within which quenching does not occur throughout the rated (or maximum safe) current range of the coil.

To show how eq. 2 is derived, it is first noted that the energy contained in the field from current flowing in a coil at time t is $$W(I) = \tfrac{1}{2} L I^2(t), \qquad (4)$$

where W(t) is the energy present in a coil undergoing ramping at time t. The power delivered to the field of a non-dissipative electromagnet as a function of time is $$P(t) = dW/dt. \qquad (5)$$

Using the relationship $$dW/dt = (dW/dI) \times (dI/dt), \qquad (6)$$

it can be shown that $$P(t) = L I(t)(dI/dt), \qquad (7)$$

or alternately, $$d(t)dT = [P(t)/L]dt. \qquad (8)$$

Integrating this equation from starting time $t_o$ to t, at which times the current is $I_o$ and I(t), respectively, the equation for I(t) as a function of elapsed time $t-t_o$ is $$I^2(t) = I_o^2 + (2P(t)/L)(t-t_o) \qquad (9)$$

Thus, if the power P(t) that is delivered to the field of the electromagnet is to be kept at a constant value $P_o$, and the initial current $I_o=0$ at time $t_o$, the current to be delivered to the coil, in accordance with the first embodiment of the invention (eq. 2), should rise in proportion to the square root of elapsed time t. Of course, if the current $I_o$ is nonzero at the time selected as $t_o$, the current delivered to the coil should rise in accordance with the more general equation for $I^2(t)$.

For best results in employing this embodiment of the invention, it is desirable to select $P_o$ to be as large as possible. However, for a superconducting coil, if too large a value of $P_o$ is selected, there is a risk that the coil will quench. An experimental procedure may be used to determine a maximum safe value of $P_o$ as follows. A power supply having a current limiter is connected to the coil, and a maximum magnitude of coil current is selected. (Of course, the coil's maximum rated current limit should be at or above the selected maximum magnitude of coil current.) (For the purpose of explaining the remainder of the procedure for determining $P_o$, we shall assume, without loss of generality, that all of the currents and voltages have positive values, so that we need not continually refer to their "magnitudes.")

Let us assume, for example, that the coil is rated at 80 amperes, and the maximum current selected is 70 amperes. The power supply is connected to the coil and the current limit is set for the selected maximum coil current, which for this example, is 70 amperes. Then, the output of the power supply is set at a fixed voltage (typically, but not necessarily, 10 volts). The coil current will ramp up linearly with time, and the total power will reach 700 watts just before the stabilization point. This process is repeated, with a voltage increased to a value higher than the originally applied voltage—e.g., 15 volts for the purpose of this example. At 15 volts, the coil will ramp to the 70 ampere current limit (or whatever value of current limit was selected) at a 50% faster rate. Ramping at successively higher voltages is performed, until the coil is observed to quench before the coil draws the full amperage (i.e., the set limit) from the power supply. The presence of quenching is made evident by a dramatic drop in the current flowing through the coil. The maximum power $P_o$ is computed as the current through the coil at the quench point multiplied by the applied voltage.

Alternately, the current and ramp rate of a coil used with other ramping systems can be observed while the coil is in use with the other ramping system. Inevitably, the coil will be observed to quench while in use. The value of current and voltage at the quench point can simply be noted when this occurs. The maximum power $P_o$ can be computed from the product of these quantities.

Figure 7:
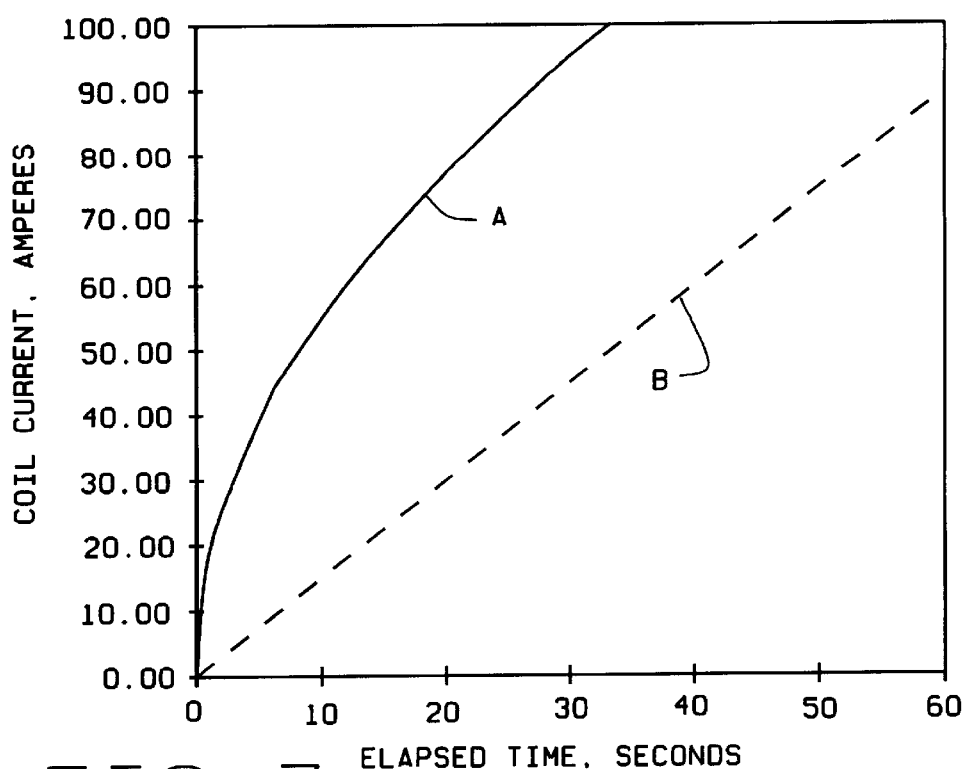
FIG. 7 is a graph of coil current as a function of time for constant power ramping from zero amperes to 100 amperes with P=3 kW, as compared to constant voltage ramping with V=28.5 volts, for a particular superconducting coil having a measured inductance of 20 Henries.
Figure 8:
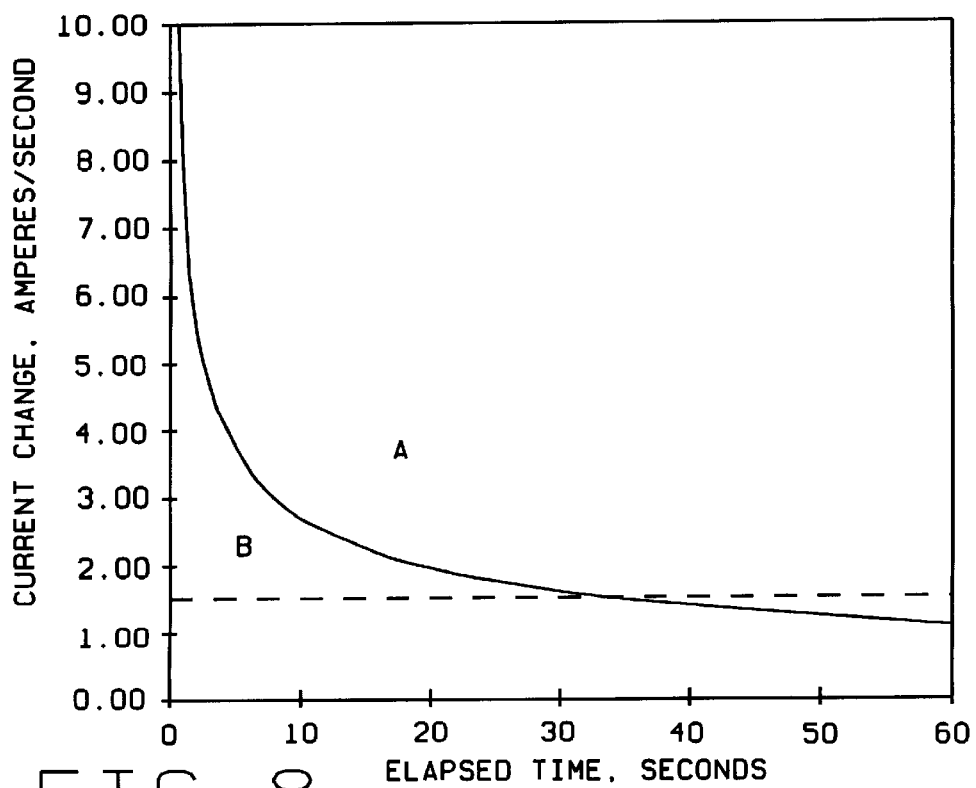
FIG. 8 is a graph of the ramping rates dI/dt corresponding to the graph of FIG. 7.

A dramatic and unexpected decrease in time required to reach a final selected current I accrues when superconducting coils are ramped in accordance with the first embodiment of the invention. Comparison of the time required for this method versus the time required for prior art constant-voltage ramping is illustrated generally in FIGS. 1–6, which show current as a function of time for constant-power ramping curves A and constant-voltage ramping curves B. A more specific example is shown in FIG. 7, which is a graph of current as a function of time in a particular superconducting coil having an inductance of 20 Henries. Constant power ramping (curve A) from zero amperes to 100 amperes was accomplished in approximately 32 seconds with P=3 kW. On the other hand, constant voltage ramping (curve B) with V=28.5 volts did not reach this level of current after 60 seconds. (The voltage selected for this example was that which provided the maximum ramp rate for constant voltage ramping without quenching the coil.) FIG. 8 is a graph of the corresponding ramping rates dI/dt for constant-power ramping A and constant-voltage ramping B for the coil used to obtain the corresponding curves A and B in FIG. 7. As illustrated in FIGS. 7 and 8, constant power ramping can be particularly effective at producing rapid changes in coil current at relatively low current levels, where the rate of current change is greatest. FIG. 8 shows that the rate of current change for constant power ramping eventually falls below that of constant voltage ramping. However, FIG. 7 shows that constant power ramping can achieve such a large "jump start" that an advantage over constant voltage ramping could be maintained, if required, for a substantial period beyond the time at which the magnitudes of the first derivatives of curves A and B in FIG. 8 cross.

Experimentally, it has been shown that constant power ramping in accordance with this aspect of the invention is effective, and that larger currents can be reached in a given coil much earlier than by the constant voltage method.

However, the constant-power ramping method tends to produce more conservative ramping than might otherwise be achievable. Thus, in accordance with another embodiment of the invention, a charging rate is provided to produce even more rapid ramping of current in accordance with the equation $$I(t)=[(2/3)(Q/k_f)(t-t_o)+I_o^{(3/2)}]^{(2/3)}, \quad (10)$$

where Q is a quench factor (which is treated as a constant), $k_f$ is an experimentally determined constant, and $I_o$ is an initial value of current at time $t_o=0$. Providing current in accordance with this equation more optimally minimizes heat losses within an electromagnet that may otherwise cause it to quench, while at the same time also minimizing the time required to change the current in the magnet by a given amount. This method of charging an electromagnet also advantageously compensates for both self-generated eddy current losses and self-generated high field effects.

For the purposes of this embodiment of the invention, it is necessary to determine only the ratio $Q/k_f$ in eq. 10, not the individual values Q and $k_f$. This can be done by direct comparison with the equation $$I^2(t)=I_o^2+(2P(t)/L)(t-t_o) \quad (11)$$

by setting both $t_o$ and $I_o^2$ to zero to give:

$$I_2(t)=2P_o t/L. \quad (12)$$

(In eq. 12, we have substituted a fixed value $P_o$ for $P(t)$, the fixed value being determined in the same manner as for the preceding embodiment of the invention.) Both $P_o$ and L are known. Several different values of I are selected, preferably equally spaced between zero amperes and the maximum required coil current (which should be the same as the current used to determine $P_o$) but excluding zero. For example, if the maximum required current is 70 amperes, four different currents I(t) are selected: 17.5, 35, 52.5, and 70 amperes. The equation $$I^2(t)=2P_o t/L \quad (13)$$

is then solved to obtain the values of t that correspond to the selected values of I(t). Then, the values of I(t) and t are substituted into the eq. 10, where, without loss of generality, $I_o$ and $t_o$ are again set to zero. Eq. 10 can then be rearranged to:

$$Q/k_f=(3/2)I^{(3/2)}(t)/t, \quad (14)$$

from which several different values of Q/kf are determined corresponding to different pairs of I(t) and t. One of the values of $Q/k_f$ is selected for use in this embodiment of the invention, depending upon the level of performance required. Higher values of $Q/k_f$ correspond to higher performance (more rapid ramping), but may result in occasional quenching. Lower values will result in lower performance, but less likelihood of quenching. Thus, some degree of flexibility is provided in this embodiment of the invention, and it is possible to operate in a range closer to the physical limits of the coil.

The different values of $Q/k_f$ are obtained because the equation for $Q/k_f$ is an approximation, rather than an exact description, of the quenching behavior of the coil. Individual values of $Q/k_f$ will have significant errors. Thus, either one of the experimentally-derived values is selected (as described above) or a statistical best fit can be used. Although data could be fitted to a more complex model for quenching, fitting large numbers of experimental values into a model is usually not advisable, because of the hazards associated with repeated quenching of coils.

From Faraday's Law of Induction, it can be shown that the magnitude of the eddy current density $J_e$ in a coil and its surroundings is given by $$J_e=k\times(dI/dt), \quad (15)$$

where I is the total current flow, and k is a constant that depends upon the materials and geometry of structures around the coil. The power density per unit volume for eddy current dissipation is thus given by $$P_e=J_e^2\rho, \quad (16)$$

where $\rho$ is the resistivity of the material. (The bobbin and support structures are not superconducting and will have a finite value of $\rho$.) Therefore, the total power $P_d$ dissipated in the material surrounding the coil due to eddy currents will be $$P_d=k'(dI/dt)^2, \quad (17)$$

where k' is a constant that depends upon the structure, materials, geometry, and other physical characteristics of the electromagnet.

The immersion field of any single wire in a coil is caused both by its own current and by the current in the other turns in the same coil. Typically, these will each be proportional to the total current I in the coil. Determining current levels and current change rates that may cause a superconducting coil to quench is generally very difficult, because not all turns of a coil are likely to have the same thermal conductivity to a cold reservoir, nor will materials in their vicinity be likely to have the same thermal capacities. Therefore, it is common practice, in superconducting coil design, to use finite-element programs to calculate the fields present, at least for single coils having a standard geometry or for simple arrays of coils.

For another embodiment of the invention (See Eq. 10), we have chosen to use a quench factor Q having a simple linear dependence on the coil current I, representing the high field effect. When this is combined with the eddy current effect, the total dependence of Q can be given either by adding or by multiplying the two effects. An approximation sufficient for purposes of this invention can be obtained by using a model in which the effects are multiplied. The quench factor is then given by the equation:

$$Q=k\times k'P_d\times I = k_f\times I\times(dI/dt)^2, \quad (18)$$

where $k_f$ is an overall empirically-determined constant. If it is assumed that Q and $k_f$ are approximately constant, this equation can be rearranged into the equation $$I^{1/2}dI=(Q/k_f)^{1/2}dt \quad (19)$$

and integrated from time $t_o$ to t to give the ramping equation given above (Eq. 10) for this embodiment of the invention.

Figure 9:
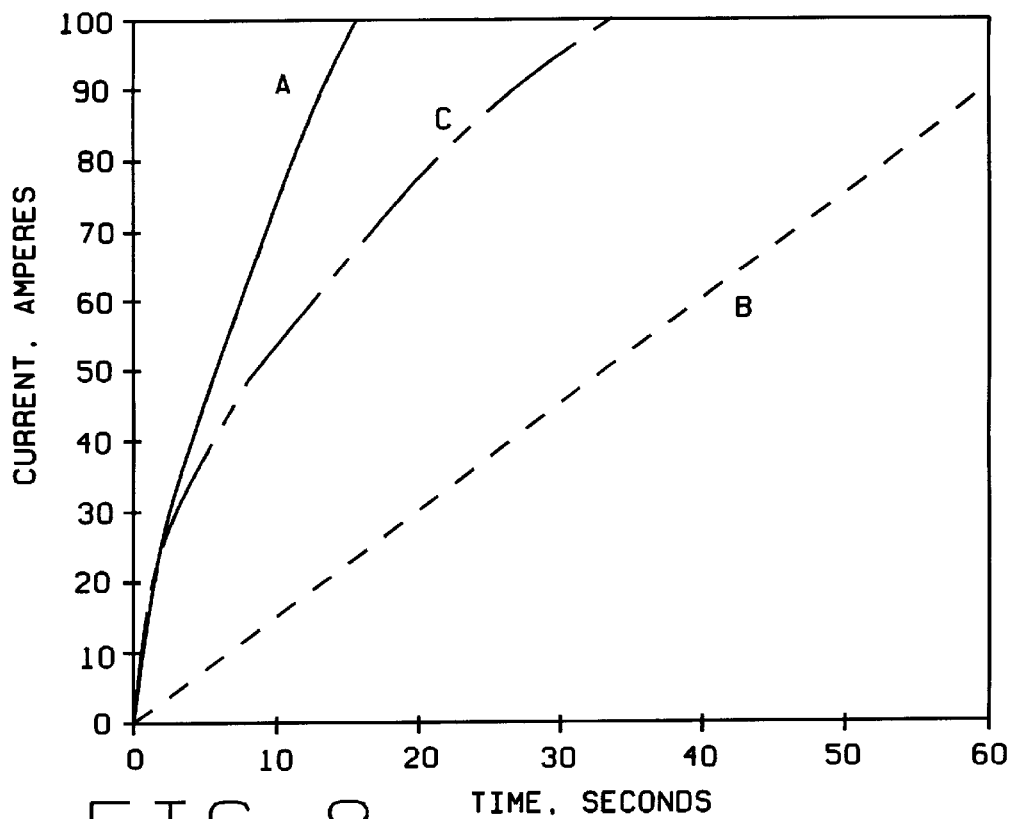
FIG. 9 is a graph of coil current as a function of time for the same coil as FIGS. 7–8 for another embodiment of the invention in which ramping is controlled to minimize heat losses.

A plot of I ramped in accordance with this embodiment of the invention is shown in FIG. 9. The plotted example A is for the same coil described in conjunction with FIGS. 7–8, i.e., a 20 Henry superconducting coil with a maximum ramp rate without quenching of 1.5 A/s at 100 A. Particular values of the constant quantity $Q/k_f$ were chosen to meet the expected quench conditions for this coil. Different values for this constant would be chosen (based on experimental values) for other coils, depending upon their size and construction, which would result in a different ramp rate for each different coil.

For comparison, FIG. 9 also shows, plotted on the same scale, a constant power ramping curve C and a constant voltage ramping curve B. In the plotted examples, the power law for the rise of current with time is ⅔ for this embodiment of the invention, as compared with ½ for the constant power case and 1 for the constant voltage case. In practice, the experimental determination of $Q/k_f$ allows higher scaling and therefore more rapid approach to maximum current to be achieved for many coils with ramping provided in accordance with eq. 10.

It is not necessary to assume that the quench dependence is linear either in I or as a product with $(dI/dt)^2$. Additional powers of the factors I and dI/dt could be included in the ramping model and/or used in different terms, with coefficients determined by finite element calculations and/or fitting coefficients to the observed behavior of a given system. One such equation might be determined, for example, from a quench function Q where the k coefficients are taken as constants, and Q is given in the form of a differential equation in I(t):

$$Q = k_1 \times I(t) + k_2 \times I^2(t) + k_3 \times (dI(t)/dt) + k_4 \times (dI(t)/dt)^2 \quad (20)$$

More terms can be added in increasing powers of I and dI(t)/dt (as well as terms involving products of powers of I and dI/dt), to obtain increasingly efficient ramping. However, a simpler ramping rate such as described in conjunction with the other embodiments of the invention is usually satisfactory and preferred, for reasons of simplicity and practical applicability.

Some other equations can be derived for special cases. For example, it is well-known that common superconductors obey the intrinsic equation stated above as eq. 1, which relates the critical magnetic field $H_c$ at a temperature T, to a critical temperature $T_c$ above which the material will not be a superconductor. It can be shown that a current ramping rate given by $$I(t) = A_1 - (B_1 t + C_1)^{4/3} \quad (21)$$

will more closely match this superconducting behavior, where $A_1$, $B_1$, and $C_1$ are constants. However, the applicability of the intrinsic equation for $H_c$ must first be determined before it can be assured that this ramping rate is advantageous for a given coil system.

Any of the foregoing embodiments may be used in conjunction in a complementary synchronization technique in which one coil pulls and a second coil pushes a magnetic object between the coils. Much faster ramping of current for complementary synchronization is made possible by the use of constant power ramping (or of one of the other inventive methods) than with constant voltage ramping. This increased speed is possible because the push-pull coil (also called a boost, supplementary, or subsidiary coil) is used with a much smaller current than the partner coil on the same axis. One coil, the main coil, always pulls the "seed" or implant. The subsidiary coil functions in two different ways at two different times in a step—as a boost coil, helping the main coil by pushing in the direct it pulls, and secondly as a halt coil, opposing the main coil by pulling back on the implant. With the inventive methods of ramping the coils (and especially with constant-power ramping), the coils can operate in a low current, high ramp rate mode, making control much faster than with constant voltage ramping and much safer and more suitable for servo control, while at the same time avoiding quenching of the coils.

Figure 10:
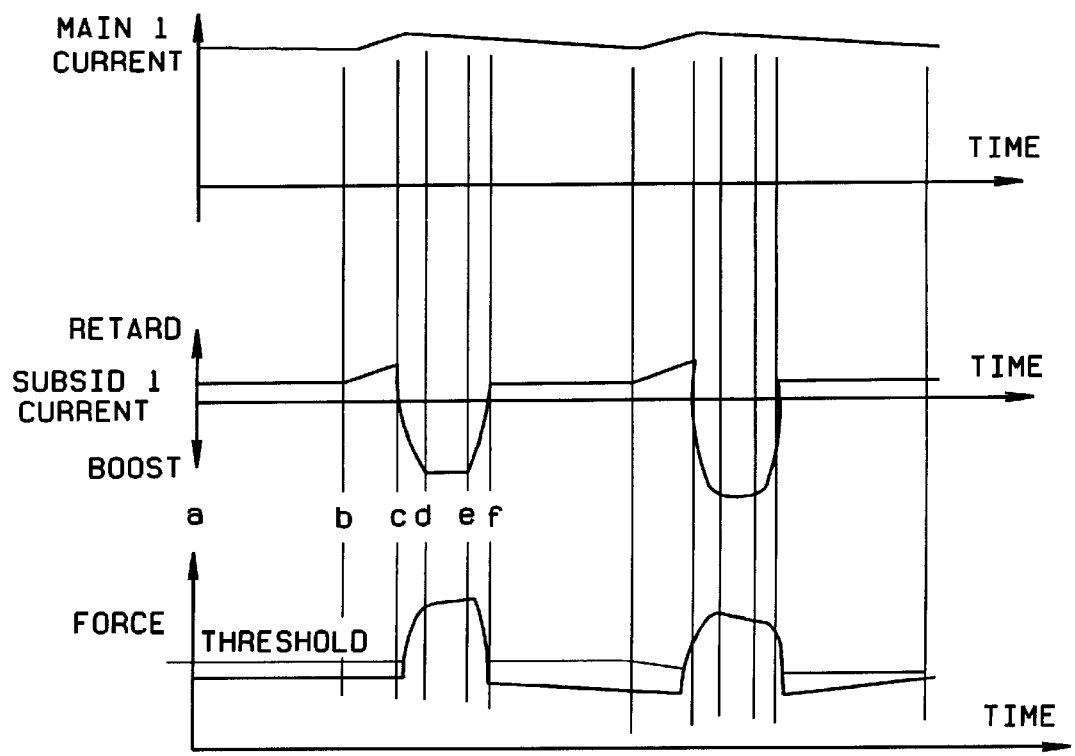
FIG. 10 is a representation of an application of the inventive current ramping methods described herein to control coil pairs operated in force opposition to deliver medication or therapy to a patient.

To explain how the inventive ramping methods may be employed in another practical system, two or more coils provided in pairs can be operated in force opposition to control a magnetic "seed" that can be used to deliver medication or therapy to a selected portion of body tissue in a patient. After motion of the seed is started, the push-pull coil, through which small currents flow, is changed from opposition force to addition force relative to the main pulling coil. FIG. 10 depicts such operation, and illustrates that great changes in force on a seed can occur very rapidly. At time a, the main coil has a current generating a magnetic field that pulls on the magnetic object, while the subsidiary (push-pull) coil has a current generating a magnetic field that opposes this pull. At time b, the currents in the coils are ramped slightly to readjust from the previous step, and to prepare for another ramp of current that starts at time c. (When moving a magnetic seed from one place to another, current adjustment provides magnetic fields that define a proper starting direction for the next motion of the magnetic seed without actually causing motion of the seed. Such adjustments are already explained in our other previously mentioned patent applications.) In this ramp, the main coil remains at the same current I from time c to time f, while the subsidiary coil ramps rapidly in constant power mode (i.e., in accordance with eq. 2) through zero from its value at time c to a value at time d where it is assisting the pull of the main coil. Since this ramp occurs at low currents, it can be done extremely rapidly in constant power mode. At time e, the previous ramping step is reversed, and the two coils are quickly brought into opposition again. If the prior art constant voltage ramping is used, instead, the subsidiary coil current would ramp at a constant slope limited by the maximum safe value of voltage that can be applied to the coil at maximum current. This prior art usage would result in much slower changes to the forces on the magnetic object.

The operation described in the coil pair case above can be compared to having two opposing springs acting on an object. The closest, push-pull coil can be compared to a spring that can change its spring constant rapidly, because of the large force change associated with a small current change. The coil pair system is "loaded," and then the current in the push-pull coil is rapidly changed and reversed in direction. Because of the "preload," it is possible to safely have the main current much closer to the threshold value for seed movement, so that the force impulse can be effectuated very rapidly.

Implementation of the inventive ramping methods may be achieved with a combination of software and/or firmware and hardware, in which the software and/or firmware include constants for the ramp equation or equations and current values are calculated in accordance with the equation or equations. The hardware converts the calculated current values into actual electric currents. For superconducting magnet control, it is necessary in some applications (such as the seed application described above) to be able to apply both positive and negative currents to the coil at different times. The software functions provided below, which are written in the C++ programming language and which are self-documenting, provide a solution to this problem. (These routines are copyrighted by Stereotaxis, Inc. All rights under the copyright are reserved, except that copying and republication solely in conjunction with the publication and dissemination of this patent is expressly permitted.)

A multiple coil system comprising multiple superconducting magnets may require temporal synchronization of the ensemble's magnet coil currents. A method of multiple coil control has been developed in our previously mentioned patent applications that scales the rate at which ramp time is accrued for an individual coil. A scaling is implemented such that the current ratios for the coils in the system are maintained throughout any ramping activity. To implement coil current control in a multiple superconducting magnet system in which positive and negative currents are required, a system of multiple, remote computer processing systems can be provided, where one system is dedicated to controlling the ramping of a single coil or pair of coils, which change currents (or "charge") in unison or in synchronization. These computer systems can communicate via a bidirectional communications interface and share a clock generated either by one of the processing systems or by a host system. The shared clock ensures that synchronization will be maintained as the various coils are charged under control of their separate systems, so that the coils reach their final, steady-state values of current simultaneously.

Figure 11:
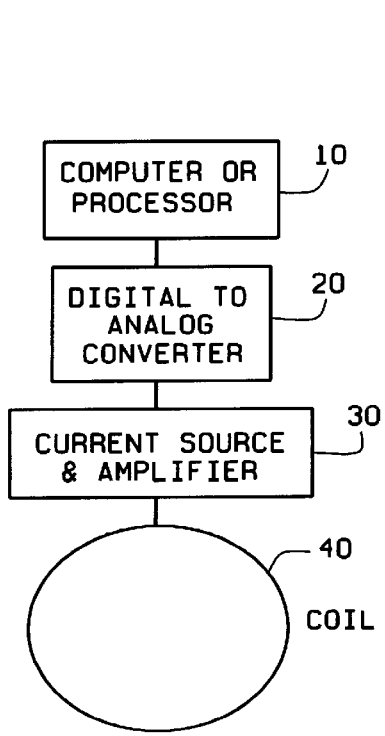
FIG. 11 is a schematic block diagram of a hardware system capable of implementing the inventive methods of current ramping described herein.

The basic hardware needed to implement the inventive ramping methods described herein is shown in FIG. 11. A computer or other processor 10 having any desired input, output, and/or display devices (not separately shown) may be used to calculate values of I(t) to be applied to coil 40. (It will be understood by those skilled in the art that the values calculated need not actually be I(t), but may instead be a related quantity that can conveniently be processed by the hardware to provide the required analog I(t) value.) The calculated values may be based upon commands and/or data input by a user, upon pre-programmed instructions, or upon data from remote sensors, or any combination thereof. The numerical values of I(t) (or the related calculated quantity) are communicated at appropriate times to digital-to-analog converter (D/A) 20, which supplies an analog signal to a (preferably pulse-width modulated) current source and amplifier 30, which, in turn, converts the analog signal into the required coil current I(t) and applies this current to coil 40.

Figure 12:
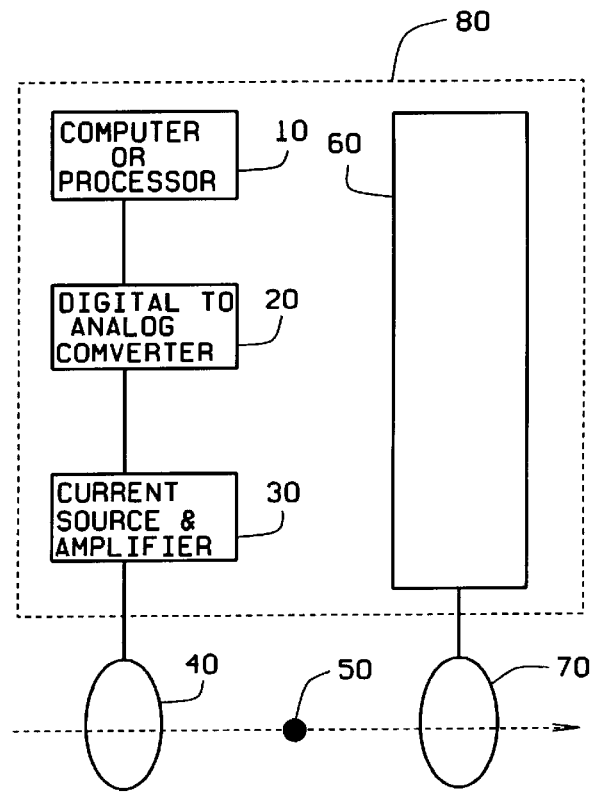
FIG. 12 is a schematic block diagram of a hardware system having two electromagnetic coils operating on a single magnetic seed.
Figure 13:
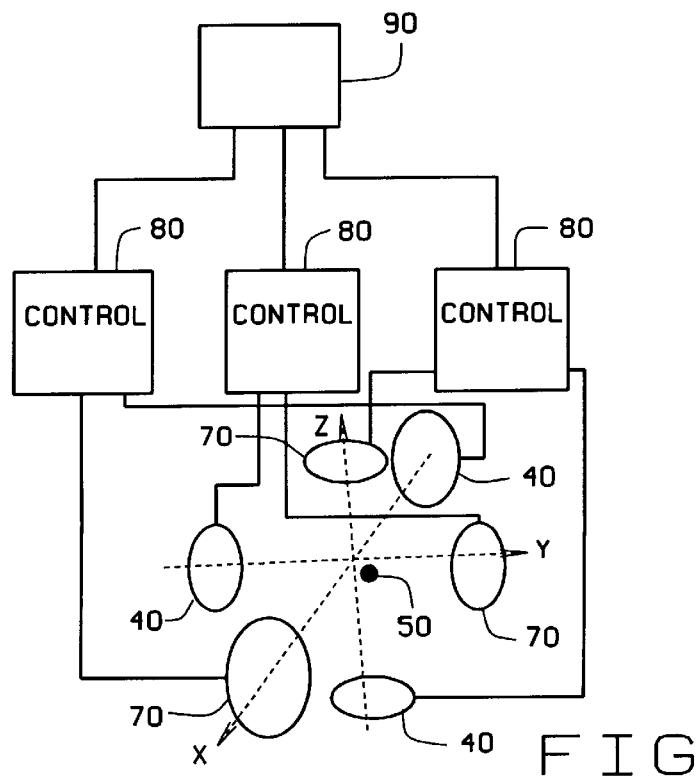
FIG. 13 is a schematic block diagram of a hardware system comprising a plurality of controlled, synchronized coils operating in orthogonal directions on a single magnetic seed.

When operated in a coil pair configuration to control a seed So as shown schematically in FIG. 12, a pair of coils 40, 70 may be used. At least one of the coils (the push-pull coil 40) may be operated in accordance with the system that was described in conjunction with FIG. 10. The other coil (main coil 70) is operated by a system 60 supplying current to it, which is also preferably a system such as that described in conjunction with FIG. 10. The control apparatus 80 is defined, for convenience, to be those components within the dashed box in FIG. 12. The two coils 40, 70 are axially aligned, and exert a magnetic force on a magnetic seed 50 disposed between the coils. (The seed is illustrated on the axis X, but need not be so positioned.) FIG. 13 shows schematically how a plurality of coils 40, 70 may be located, preferably on orthogonal axes X, Y and Z, to control the orientation of a magnetic seed 50 in three dimensions. A processor 90 is used to synchronize the control apparatuses 80 so that the changing currents in the coils are synchronized to provide a desired trajectory and rate of movement of seed 50.

It will be observed that the inventive ramping methods can be used in numerous applications in addition to those described above.

It will be understood that the above description is intended for exemplary purposes only, and that many modifications to the inventive methods will be readily apparent to one skilled in the art without departing from the spirit of the invention. Therefore, the scope of the invention should be determined by reference to the claims below, including the full range of equivalents permitted under applicable law.

Copyright Stereotaxis, Inc.

```
/*****************************************************************
* Purpose:
*    This routine is the constructor for a coil object.
*
* Error conditions:
*    If the servoamp status is detected to be bad, the
*    coil status is set to fault which disables coil ramping.
*
* Notes:
*    Base classes of the coil class are servoamp (control and monitoring of
*    the actual hardware servoamplifier) and ramp_model (mathematical
*    description of coil current ramp characteristics).
*****************************************************************/
coil::coil{                                      //f coil class constructor
                    helmet_coils ampid           //i id of this amp
                    }
                    : servoamp(ampid),           //b base class constructor call
                    ramp_model()                 //b base class constructor call
{
    target_current = 0.0;                        // initialize object values . . .
    if(servoamp::get_actual_current(current_now) == AMP_FAULT) // Check for current already on the coil
        current_now = 0.0;
    total_ramp_time = 0.0;
    net_event_time = 0.0;
    ramp_scale = 1.0;
    ramp_dir = RAMP_UP;
    coil::status = COIL_OK;          // Init coil status
```

-continued

Copyright Stereotaxis, Inc.

```
/************************************************************
 * Purpose:.
 *   The routine is used to set the private value of the ramp scale. The
 *   ramp scale is used to scale the rate of increase of coil current.
 * Error conditions:
 *   Acceptable ramp scale values are greater than or equal to zero and
 *   less than or equal to one. If the value passed in is not within these
 *   bounds, a fault value is returned.
 ************************************************************/
int                                      //r returns coil status
coil::set_ramp_scale(                    //f set the ramp scale
               double scale              //i value to use for ramp_scale
               )
{
    if (!CHECK_RAMP_SCALE(scale))        // check if value is in bounds
    {
        Log::Write(INVPARAM, "WARNING::set_ramp_scale - Ramp scale %d.%03d out of bounds. Setting to valid value.\n",
             (int)scale, (int)(scale*1000.0));
        if (scale <= MIN_RAMP_SCALE)
            ramp_scale = MIN_RAMP_SCALE;
        else if (scale > MAX_RAMP_SCALE)
            ramp_scale = MAX_RAMP_SCALE;
        return(COIL_FAULT);
    }
    ramp_scale = scale;                  // Passed the conditionals, so set
                                         // the ramp_scale.
    return(COIL_OK);
}
/************************************************************
 * Purpose:
 *   This function initiates a charge sequence to ramp the coil to a given
 *   target current using the given ramp scale. Any previous charging request
 *   is over-written.
 *
 * Error conditions:
 *   If the coil is in a Fault state, nothing is done and a fault value
 *   returned.
 ************************************************************/
int                                      //r return coil status
coil::start_charge(                      //f initiate a charge event
               double current,           //i target current to ramp to
               double scale              //i scale to ramp to target current with
               )
    if (coil::status & COIL_FAULT)
    {
        Log::Write(INVPARAM, "\nWARNING: Attempt to start charging coil with COIL_FAULT set");
        return(COIL_FAULT);              // return COIL_FAULT
    }
    stop_charge();                       // stop present charge
    set_ramp_scale(scale);
    set_target_current(current);
    if(target_current < current_now)     // set ramp direction
        ramp_dir = RAMP_DOWN;
    else
        ramp_dir = RAMP_UP;
    time_last_update.set(THE_PRESENT);   // reset charge start time to now
    coil::status |= COIL_CHARGING;       // set coil state
    return(COIL_OK);
/************************************************************
 * Purpose:
 *   This function turns off coil charging. Current already on the coil is
 *   maintained as steady state.
 ************************************************************/
id                                       //r return type void, no return
il::stop_charge(void)                    //f stops coil charging
coil::status &= ~COIL_CHARGING;          // set coil status to not charging
return;
/************************************************************
 * Purpose
 *   This function updates the coil current while the coil is in a charging
 *   state. Coil current is calculated using the ramp model base class
 *   methods.
 * Error conditions:
 *   1. The ramp_model base class used to calculate coil current can return
 *      a fault which causes the charge to stop and a fault return value.
 *   2. If the current step from the previous move is greater than a predefined
```

-continued

Copyright Stereotaxis, Inc.

```
*       maximum value (MAX_CURRENT_STEP), the charge is stopped and a coil
*       fault status is returned.
*    3. Calling this routine when not charging will print a warning message,
*       and is a no-operation condition.
*************************************************************************/
t                                        //r return coil status value
il::update_current(void)                 //f update the current programmed on the coil
double time_val=0.0;
double new_current=0.0;
if (!(coil::status & COIL_CHARGING))     // Are we supposed to be charging ?
{
        Log::Write(INVPARAM, "\nWARNING: Attempt to update current when not charging");
        return(COIL_OK):                 // return, no harm done.
}
time_class time_now(THE_PRESENT);
time_class delta_time = time_now - time_last_update;   // Calculate the change in time from
                                                       // the last update_current() call
double delta_sec;
if (scale_ramp_time(delta._time.get(TC_SEC), ramp_scale, delta_sec)==RAMP_MODEL_FAULT)
{
        Log::Write(INFORMATIONAL, "update_current: scale_ramp_time failed\n");
        stop_charge();
        return(COIL_FAULT);
}
if (ramp_dir == RAMP_UP)
     time_val = (total_ramp_time + delta_sec);
else
     time_val = (total_ramp_time - delta_sec);
if (calculate_ramp_value(time_val, new_current)==RAMP_MODEL_FAULT)
{
        Log::Write(INFORMATIONAL, "update_current: calculate_ramp_value failed\n");
        stop_charge();
        return(COIL_FAULT);
}
double delta_I = (new_current - current_now);          // Calculate change in current from
                                                       // present settings and scale it
if (fabs(delta_I) > MAX_CURRENT_STEP)
{
        Log::Write(INVPARAM, "ERROR: coil::update_current() - MAX_CURRENT_STEP exceeded while charging/n"):
        stop_charge();
        return(COIL._FAULT);
}
if (ramp_dir == RAMP_UP)                 // Check for ramping up
        if (new_current >= target_current)   // Have we reached target_current?
        {
            set_current(target_current);     // If so, set current=target current
            current_now = target_current;    // Update private copy of current
            stop_charge();                   // Stop the charging.
            calc_ramp_time(target_current, 1.0,   // Set total ramp time for target current
                   total_ramp_time);
        }
        else                             // Otherwise, set current to what
        {
            set_current(new_current):        // was calculated and update
            current_now = new_current;       // current_now and ramp_time.
            total_ramp_time = time_val;      // Update total ramp time
        }
    else                                 // Check for ramping down
    {
        if (new_current <= target_current)   // Have we reached target_current?
        {
            set_current(target_current);     // If so, set current=target current
            current_now = target_current;    // Update private copy of current
            stop_charge();                   // Stop the charging.
            calc_ramp_time(target_current, 1.0,   // Set total ramp time for target current
                   total_ramp_time);
        }
        else                             // Otherwise, set current to what
        {
            set_current(new_current);        // was calculated and update
            current_now = new_current;       // current_now and ramp_time.
            total_ramp_time = time_val;      // Update total ramp time
        }
    }
    time_last_update = time_now:         // Update ramp clock time
    return(COIL_OK);
/*************************************************************************
```

-continued

Copyright Stereotaxis, Inc.

```
*   Purpose:
*     Sets the value of the target current to ramp to during the next
*     charging sequence.
*
* Error conditions:
*   1. If the target current is not within the predefined coil current limits,
*      a message is printed and a coil fault value is returned.
***************************************************************************/
int                                      //r returns coil status
coil::set_target_current(                //f sets the value of the target current
                double current          //i value to ramp coil current to
                )
{
    if (IS_CURRENT_IN_BOUNDS(current))
        target_current = current;
    else
    {
        Log::Write(INVPARAM, "WARNING: Attempt to set target current to out-of-bounds value\n");
        Log::Write(INVPARAM, "         Target Current was NOT changed!");
        return(COIL_FAULT);
    }
    return(COIL_OK);
/***************************************************************************
* Purpose:
*   This routine provides a method of reading the actual (not programmed)
*   coil current_on the coils
*
* Error conditions:
*   1. If the servoamp returns an error status, the corresponding coil
*      status is returned.
***************************************************************************/
nt                                       //r Coil status is returned
coil::get_coil_current(                  //f Get and return actual coil current
                double& current         //o Set to value of current read
                )
    if (servoamp::get_actual_current(current) == AMP_FAULT)
        return(COIL_FAULT);
    else
        return(COIL_OK);
/***************************************************************************
* Purpose:
*   This routine returns the status of the coil. The coil's status is held
*   in the private member status.
* Error conditions:
*   None.
***************************************************************************/
nt                                       //r coil status is returned
coil::get_coil_status(                   //f return coil status
void)
    return(coil::status);
```

```
//-------------------------------------------------------------------------
//                       (C)opyright Stereotaxis, Inc.
//-------------------------------------------------------------------------
/***************************************************************************
* Purpose:
* This source file implements the ramp_model class used for calculating
* coil currents and ramp times. It allows the user to set equation
* coefficients and exponents to describe the relationship between time
* and current mathematically.
*
* Version: 1.10    Date:
*
* Hazard Related:
*    Yes
*
* Notes:
* 1. In its present form, the class WORKS ONLY for equations with exponents
*    of a single power or zero. This avoids the need to solve a non-linear
*    equation to find the ramp time given a current value.
*
***************************************************************************/
```

-continued

```
/****************************************************************
 * Purpose:
 *   ramp_model() function is a constructor for a ramp_model object. It is
 *   called with no arguments. Initialization of class members must be
 *   performed using other member functions.
 *
 * Error conditions:
 *   None
 *
 ****************************************************************/
ramp_model::ramp_model()                //f Creates an empty instance of the
ramp_model class
{
    ramp_coef = 0.0;                    // Initialize values to zero
    ramp_exp = 0.0;
}
/****************************************************************
 * Purpose:
 *   set_ramp_coef function sets the coefficient values the
 *   ramp equation.
 *
 * Error conditions:
 *   Negative coefficient values are not allowed, they may cause problems
 *   when used in the pow() math library function which uses these values
 *   for calculations.
 *
 ****************************************************************/
int                                     //r return status flag
ramp_model::set_ramp_coef(              //f sets ramp equation coefficient
                double coef             //i coefficient of ramp model term
                )
{
    if (coef <= 0.0)
    {
        Log::Write(INVPARAM, "ERROR: ramp_model::set_ramp_coef()- Coefficient value
MUST be positive\n");
        ramp_coef = 0.0;
        return(RAMP_MODEL_FAULT);
    }
    else
        ramp_coef = coef;
    return(RAMP_MODEL_OK);
}
/****************************************************************
 * Purpose:
 *   get_ramp_coef() function returns a pointer to a copy of the present
 *   ramp equation coefficient values.
 *
 * Error conditions:
 *   Memory allocation for the new array could fail, in which case the pointer
 *   returned is set to NULL.
 ****************************************************************/
double                                  //r return the coefficient value
ramp model::get_ramp_coef(              //f gets ramp equation coefficient
    void)
{
    return (ramp___coef);
}
/****************************************************************
 * Purpose:
 *   set_ramp_exp function sets the exponent value of the ramp equation.
 *
 * Error conditions:
 *   Negative values for exponents are not allowed. This ensures that some
 *   error conditions will not arise when using these values in pow() calls.
 *
 ****************************************************************/
int                                     //r return success or unsuccess
ramp_model::set_ramp_exp(               //f set ramp equation exponent
                double exp              //i exponent value to use
                )
{
    if (exp <= 0.0)
    {
        Log::Write(INVPARAM, "ERROR: ramp_model::set_ramp_exps()- Negative exponent
values are NOT allowed\n");
        ramp_exp = 0.0;
        return(RAMP_MODEL_FAULT);
    }
```

```
        else
            ramp_exp = exp;
        return(RAMP_MODEL_OK);
}
/****************************************************************************
* Purpose:
*    get_ramp_exp() function returns a pointer to a copy of the present
*    ramp equation exponent values.
*
* Error conditions:;
*    Memory allocation for the new array could fail, in which case the pointer
*    returned is set to NULL.
*
****************************************************************************/
double                              //r return a pointer to a copy of the
exponents
ramp_model::get_ramp_exp(           //f return present ramp exponents
    void)
{
    return (ramp_exp);
}
/****************************************************************************
* Purpose:
*    This function calculates a current value for for a time using the ramp
*    model equation defined by the ramp exponents and coefficients.
*
* Error conditions:
*    None.
*    The possibility of the pow function causing an error is eliminated by
*    checking the values of the exponent when it is set in set_ramp_exps().
*    NULL variable pointers or bad values are trapped by checking the status of
*    the exponent and coefficient.
*
****************************************************************************/
int                                 //r return value, fault if error in
calculation
ramp_model::calculate_ramp_value(   //f calculate a current value
                    double time_val,    //i time for which to calc
                    double& ramp_val    //m calculated current value
                    )
{
    if ((ramp_coef <= 0.0) || (ramp_exp <= 0.0))
    {
        Log::Write(INVPARAM, "ERROR:ramp_model::calculate_ramp_value - coefficient
or exponent is BAD\n");
        return(RAMP_MODEL_FAULT);
    }
    int value_sign;
    if(time_val < 0.0)              // This method of stripping the sign from
the value
        value_sign = -1;            // is used to avoid errors for functions
that are
    else                            // undefined for values < 0. This allows
the ramp
        value_sign = 1;             // function to be symetric about zero.
    time_val = fabs(time_val);      // Make sure value is positive
    ramp_val = ramp_coef = pow(time_val,ramp_exp);
    ramp_val *= value_sign;         // account for original value sign
    return(RAMP_MODEL_OK);
}
/****************************************************************************
* Purpose:
*    This function calculates a ramp time value for a current using the ramp
*    model equation defined by the ramp exponent and coefficient.
*
* Error conditions:
*    None.
*    The possibility of the pow function causing an error is eliminated by
*    checking the values of the exponents and coefficients before the pow call.
*
****************************************************************************/
int                                 //r fault if exps or coefs are
not set
ramp_model::calc_ramp_time(         //f calcs a ramp time for a
                                    // current and ramp scale
                    double current,     //i current to calc time for
                    double time_scale,  //i ramp scale
                    double &ramptime    //o time to ramp to current at
ramp_scale
```

```
                )
{
    if ((ramp_coef <= 0.0) || (ramp_exp <= 0.0))
    {
        Log::Write(INVPARAM, "ERROR:ramp_model::calculate_ramp_time – coefficient or
exponent is BAD\n");
        return(RAMP_MODEL_FAULT);
    }
    if (time_scale < MIN_RAMP_SCALE)
        time_scale = MIN_RAMP_SCALE;
    double isign;
    if(current < 0)
        isign = –1.0;
    else
        isign = 1.0;
    ramptime = pow(fabs(current)/ramp_coef,1/ramp_exp) / time_scale * isign;
    return(RAMP_MODEL_OK);
}
/*****************************************************************************
 * Purpose:
 *   This function calculates the ramp time between two currents using the ramp
 *   model equation defined by the ramp exponent and coefficient.
 *
 * Error conditions:
 *   An error from calc_ramp_time() is checked for and a fault condition
 *   returned if detected.
 *
 *****************************************************************************/
int                                      //r fault if exps or coefs are not
set
ramp_model::calc_ramp_time (             //f calc ramp time between two
currents
                double start_current,    //i starting current
                double end_current,      //i ending current
                double time_scale,       //i ramp scale to charge with
                double &ramptime)        //o time it takes to go from start
                                         // to end current
{
    if ((ramp_coef <= 0.0) || (ramp_exp <= 0.0))
    {
        Log::Write(INVPARAM, "ERROR:ramp_model::calculate_ramp_time – coefficient or
exponent is BAD\n");
        return(RAMP_MODEL_FAULT);
    }
    double t1, t2;
    if (time_scale==0.0)    // Trap for zero conditions
        ramptime = 0.0;     // that would cause bad return values
    else
    {
        int status1 = calc_ramp_time (start_current, *1.0, t1);
        int status2 = calc_ramp_time (end_current, 1.0, t2);
        if(status1 || status2)
            return(RAMP_MODEL_FAULT);
        ramptime = fabs (t2 – t1) / time_scale;
    }
    return(RAMP_MODEL OK);
}
/*****************************************************************************
 * Purpose:
 *   This routine scales a ramp time according to the scale passed in and the
 *   ramp model equation.
 *
 * Error conditions:
 *   If the ramp equation is not valid, an error is returned and scaled_time
 *   is set to zero.
 *
 * Notes:
 *   The time_scale input is based on the following general equation type:
 *      I(t) is proportional to (t*time_scale)^(ramp_exp)
 *
 *****************************************************************************/
int                                      //r return fault if equation
is not valid
ramp_model::scale_ramp_time(             //f Scale a given ramp time
                double time,             //i The time to scale.
                double time_scale,       //i the time scale value
                double &scaled_time      //o the scaled time value
                )
{
```

-continued

```
    scaled_time = 0.0;
    if ((ramp_coef <= 0.0) || (ramp_exp <= 0.0))
    {
        Log::Write(INVPARAM, "ERROR:ramp_model::scale_ramp_time - coefficient or
exponent is BAD\n");
        return(RAMP_MODEL_FAULT);
    }
    scaled_time = time * time scale;
    return(RAMP_MODEL_OK);
```

What is claimed is:

1. A method of rapidly changing a magnetic field having a controlled magnitude and produced by a coil, the method comprising the steps of:

(a) applying a first current of $I_1$ Amperes to the coil;
   (b) transitioning to a second current of $I_2$ Amperes applied to the coil by continuously varying the current, where $I_1 \neq I_2$; and
   (c) during at least a portion of a transition period between the application of $I_1$ and the application of $I_2$, applying a time-varying current I(t) to the coil, where dI(t)/dt varies as a function of time t, the magnitude of dI(t)/dt varying in a direction opposite to that in which the magnitude of I(t) varies.

2. The method of claim 1, wherein the applying and transitioning steps apply currents to a superconducting coil, and the step of applying a time-varying current I(t) to the superconducting coil comprises a step of varying I(t) in a manner which maintains a constant flow of power into the magnetic field of the superconducting coil.

3. The method of claim 1, wherein the applying and transitioning steps apply current to a superconducting coil, the superconducting coil has an inductance L, and further wherein the step of applying a time-varying current I(t) to the superconducting coil comprises applying a time-varying current I(t) to the superconducting coil in a manner such that $d^2I(t)/dt^2$ has a sign opposite to that of $I_1$ when I(t) has the same sign as $I_1$, and $d^2I(t)/dt^2$ has a sign opposite to that of $I_2$ when I(t) has the same sign as $I_2$, and the sign of dI(t)/dt is the same as that of the quantity $(I_2-I_1)$, and the magnitude of the first derivative of I(t) is, during the transition period, never less than, and at least sometimes greater than $|V_{max}|/L$;

where $|V_{max}|$ is a maximum voltage magnitude that can be applied to the superconducting coil at a current $|I_{max}|$ without quenching,
   L is the inductance of the superconducting coil, and $|I_{max}|$ is at least equal to the greater of $|I_1|$ and $|I_2|$.

4. The method of claim 3, and further comprising the step of applying an initial current $I_o$ through the superconducting coil at a time $t_o$, and wherein the step of applying a time-varying current to the coil comprises the step of varying I(t) in accordance with an equation:

$$I_2(t)=I_o^2+(2P_o/L)(t-t_o),$$

wherein $P_o$ represents a power delivered to or removed from the magnetic field, as the case may be, during the period between the application of $I_1$ and $I_2$, and wherein $P_o$ is constant.

5. The method of claim 4, and further comprising the steps of selecting a current limit $I_{max}$ for the superconducting coil, applying a voltage source to the coil, observing at what applied voltage $V_{max}$ the coil quenches at the selected current limit, and setting $P_o=V_{max} \times I_{max}$.

6. The method of claim 5, wherein the applied current I(t) applied to the superconducting coil is zero at an initial time $t_o$, and the step of applying a time-varying current comprises the step of increasing the applied current I(t) as elapsed time $t-t_o$ increases.

7. A method of ramping current in a superconducting coil in which the steps of claim 3 are applied to a first superconducting coil of a system comprising at least superconducting two coils, and further comprising the step of applying a constant current to a second superconducting coil of the system.

8. The method of claim 7, wherein the step of applying a constant current to the second superconducting coil comprises the step of applying a constant current to the second superconducting coil smaller than the selected final current in the first superconducting coil.

9. The method of claim 3, wherein I(t) is varied in a manner to simultaneously minimize heat losses within the superconducting coil and to minimize time required to change the applied current I(t) to $I_2$.

10. The method of claim 9, and further comprising the step of supplying the superconducting coil with an initial current $I_o$ at time $t=t_o$, and the step of applying a time-varying current comprises the step of varying the applied current I(t) as a function of time in accordance with a formula $$I(t)^{3/2}-I_o^{3/2}=[(t-t_o)K],$$

where K is a constant.

11. The method of claim 10, and further comprising the steps of:

selecting a current limit $I_{max}$ for the superconducting coil;
   applying a voltage source to the superconducting coil;
   observing at what applied voltage $V_{max}$ the superconducting coil quenches at the selected current limit;
   setting $P_o=V_{max} \times I_{max}$;
   selecting a plurality of values of current $\{(I_a, I_b, \ldots)\}$ between 0 and $I_{max}$; and
   computing a plurality of values of K each corresponding to one of the plurality of values of current.

12. The method of claim 11, wherein a value of K is selected from the plurality of values of K.

13. The method of claim 12, wherein a value of K is selected from a statistical best fit of the plurality of values of K.

14. A method of controlling current in at least a superconducting push-pull coil of a pair of superconducting coils operated in force opposition to control a magnetic seed comprising the step of applying a changing current to the superconducting push-pull coil in accordance with the method of claim 1.

15. The method of claim 14 wherein the superconducting coil pair comprises a superconducting main coil, wherein the step of changing current to the superconducting push-pull coil comprises the step of changing a direction of a force on the magnetic seed contributed by a magnetic field of the superconducting push-pull coil from an opposition force to an addition force relative to a magnetic field of the superconducting main coil.

16. The method of claim 15 wherein the magnitude of the currents flowing in the superconducting push-pull coil are smaller than the magnitude of the current in the superconducting main coil.

17. The method of claim 15 wherein the step of changing the direction of the force contributed by the superconducting push-pull coil comprises extracting or apply a constant flow of power to the superconducting push-pull coil, as the case may be.

18. A method of controlling current in a plurality of pairs of superconducting coils comprising the step of controlling currents in each of the plurality of pairs of superconducting coils in accordance with the method of claim 14, and further wherein the control of currents in each of the plurality of pairs of superconducting coils is synchronized so that each of the controlled currents maintain fixed ratios and reach a final, steady state value at the same time.

19. A method of controlling current in a plurality of pairs of superconducting coils comprising the step of controlling currents in each of the plurality of pairs of superconducting coils in accordance with the method of claim 15, and further wherein the control of currents in each of the plurality of pairs of superconducting coils is synchronized so that each of the controlled currents maintain fixed ratios and reach a final, steady state value at the same time.

20. The method of claim 1, wherein the step of applying a time-varying current I(t) to the coil comprises a step of varying I(t) in a manner which maintains a constant flow of power into the magnetic field of the coil.

21. The method of claim 1, wherein the coil has an inductance L, and further wherein the step of applying a time-varying current I(t) to the coil comprises applying a time-varying current I(t) to the coil in a manner such that $d^2I(t)/dt^2$ has a sign opposite to that of $I_1$ when I(t) has the same sign as $I_1$, and $d^2I(t)/dt^2$ has a sign opposite to that of $I_2$ when I(t) has the same sign as $I_2$, and the sign of dI(t)/dt is the same as that of the quantity $(I_2-I_1)$, and the magnitude of the first derivative of I(t) is, during the transition period, never less than, and at least sometimes greater than $|V_{max}|/L$;

where $|V_{max}|$ is a selected maximum voltage magnitude not to be exceeded across the coil at a current $|I_{max}|$, L is the inductance of the coil, and $|I_{max}|$ is at least equal to the greater of $|I_1|$ and $|I_2|$.

22. The method of claim 21, and further comprising the step of applying an initial current $I_o$ through the coil at a time $t_o$, and wherein the step of applying a time-varying current to the coil comprises the step of varying I(t) in accordance with an equation:

$$I^2(t)=I_o^2+(2P_o/L)(t-t_o),$$

wherein $P_o$ represents a power delivered to or removed from the magnetic field, as the case may be, during the period between the application of $I_1$ and $I_2$, and wherein $P_o$ is constant.

23. The method of claim 22, wherein the applied current I(t) applied to the electromagnet is zero at an initial time $t_o$, and the step of applying a time-varying current comprises the step of increasing the applied current I(t) as elapsed time $t-t_o$ increases.

24. A method of ramping current in a coil in which the steps of claim 21 are applied to a first coil of a system comprising at least two coils, and further comprising the step of applying a constant current to a second coil of the system.

25. The method of claim 24, wherein the step of applying a constant current to the second coil comprises the step of applying a constant current to the second coil smaller than the selected final current in the first coil.

26. The method of claim 21, wherein I(t) is varied in a manner to simultaneously minimize heat losses within the coil and to minimize time required to change the applied current I(t) to $I_2$.

27. A method of controlling current in at least a push-pull coil of a pair of coils operated in force opposition to control a magnetic seed comprising the step of applying a changing current to the push-pull coil in accordance with the method of claim 1.

28. The method of claim 27 wherein the coil pair comprises a main coil, wherein the step of changing current to the push-pull coil comprises the step of changing a direction of a force on the magnetic seed contributed by a magnetic field of the push-pull coil from an opposition force to an addition force relative to a magnetic field of the main coil.

29. The method of claim 28 wherein the magnitude of the currents flowing in the push-pull coil are smaller than the magnitude of the current in the main coil.

30. The method of claim 28 wherein the step of changing the direction of the force contributed by the push-pull coil comprises extracting or apply a constant flow of power to the push-pull coil, as the case may be.

31. A method of controlling current in a plurality of pairs of coils comprising the step of controlling currents in each of the plurality of pairs of coils in accordance with the method of claim 28, and further wherein the control of currents in each of the plurality of pairs of coils is synchronized so that each of the controlled currents maintain fixed ratios and reach a final, steady state value at the same time.

32. A method of controlling current in a plurality of pairs of coils comprising the step of controlling currents in each of the plurality of pairs of coils in accordance with the method of claim 27, and further wherein the control of currents in each of the plurality of pairs of coils is synchronized so that each of the controlled currents maintain fixed ratios and reach a final, steady state value at the same time.

33. A device for producing a rapidly changing magnetic field having a controlled magnitude, the device comprising:

(a) an electromagnetic coil;

(b) means for applying a first current of $I_1$ Amperes to the coil;

(c) means for transitioning to a second applied coil current of $I_2$ Amperes; and (d) means for applying a time-varying current I(t) to the coil between application of $I_1$ to the coil and application of $I_2$ to the coil, where dI(t)/dt varies as a function of time t, and the magnitude of dI(t)/dt varies in a direction opposite to that in which the magnitude of I(t) varies.

34. The device of claim 33, wherein the means for applying a time-varying current comprises means to vary the current I(t) in a manner which maintains a constant flow of power into the magnetic field of the coil.

35. A device controlling a magnetic field to control motion of a magnetic seed comprising (a) a plurality of devices in accordance with claim 34 configured to simultaneously provide a magnetic field to guide a magnetic seed; and (b) means for synchronizing currents in at least some of the coils.

36. A device controlling a magnetic field to control motion of a magnetic seed comprising (a) a plurality of devices in accordance with claim 34 configured to simultaneously provide a magnetic field to force a magnetic seed; and (b) means for synchronizing currents in at least some of the coils.

37. The device of claim 33, wherein the means for applying a time-varying current comprises means for applying the time-varying current I(t) to the coil in a manner such $d^2I(t)/dt^2$ has a sign opposite to that of $I_1$ when I(t) has the same sign as $I_1$, and $d^2I(t)/dt^2$ has a sign opposite to that of $I_2$ when I(t) has the same sign as $I_2$, and the sign of dI(t)/dt is the same that of the quantity $(I_2-I_1)$, and the magnitude of the first derivative of I(t) is, during the transition period, never less than, and at least sometimes greater than $|V_{max}|/L$;

L is the inductance of the coil, and $|I_{max}|$ is at least equal to the greater of $|I_1|$ and $|I_2|$.

38. A device for controlling a magnetic field to control motion of a magnetic seed comprising the device of claim 33, wherein the coil is a first coil; and further comprising a second coil operating in force opposition to the first coil, the first coil and second coil forming a coil pair.

39. The device of claim 38, wherein the second coil is a main coil, and the first coil is a push-pull coil, and wherein the means for varying the current I(t) comprises means for varying a direction of force on a magnetic seed between the main coil and the push-pull coil.

40. A device for controlling a magnetic field to control motion of a magnetic seed comprising (a) a plurality of devices in accordance with claim 39 configured to simultaneously provide magnetic forces on a magnetic seed; and (b) means for synchronizing currents in each of the pairs of coils.

41. A device for controlling a magnetic field to control motion of a magnetic seed comprising (a) a plurality of devices in accordance with claim 38 configured to simultaneously provide magnetic forces on a magnetic seed; and (b) means for synchronizing currents in each of the pairs of coils.

42. The device of claim 33, wherein the means for applying a time-varying current comprises means for simultaneously minimizing heat losses within the coil and for minimizing time required to transition to the second applied coil current $I_2$.

43. The device of claim 33, wherein the coil is a superconducting coil, and wherein the means for applying a time-varying current comprises means to vary the current I(t) in a manner which maintains a constant flow of power into the magnetic field of the superconducting coil.

44. The device of claim 33, wherein the coil is a superconducting coil, and wherein the means for applying a time-varying current comprises means for applying the time-varying current I(t) to the coil in a manner such $d^2I(t)/dt^2$ has a sign opposite to that of $I_1$ when I(t) has the same sign as $I_1$, and $d^2I(t)/dt^2$ has a sign opposite to that of $I_2$ when I(t) has the same sign as $I_2$, and the sign of dI(t)/dt is the same that of the quantity $(I_2-I_1)$, and the magnitude of the first derivative of I(t) is, during the transition period, never less than, and at least sometimes greater than $|V_{max}|/L$;

L is the inductance of the coil, and $|I_{max}|$ is at least equal to the greater of $|I_1|$ and $|I_2|$.

45. A device for controlling a magnetic field to control motion of a magnetic seed comprising the device of claim 33, wherein the coil is a first superconducting coil; and further comprising a second superconducting coil operating in force opposition to the first superconducting coil, the first superconducting coil and second superconducting coil forming a coil pair.

46. The device of claim 45, wherein the second superconducting coil is a main coil, and the first superconducting coil is a push-pull coil, and wherein the means for varying the current I(t) comprises means for varying a direction of force on a magnetic seed between the main coil and the push-pull coil.

47. A device for controlling a magnetic field to control motion of a magnetic seed comprising (a) a plurality of devices in accordance with claim 46 configured to simultaneously provide magnetic forces on a magnetic seed; and (b) means for synchronizing currents in each of the pairs of coils.

48. A device for controlling a magnetic field to control motion of a magnetic seed comprising (a) a plurality of devices in accordance with claim 45 configured to simultaneously provide magnetic forces on a magnetic seed; and (b) means for synchronizing currents in each of the pairs of coils.

49. The device of claim 33, wherein the coil is a superconducting coil, and wherein the means for applying a time-varying current comprises means for simultaneously minimizing heat losses within the superconducting coil and for minimizing time required to transition to the second applied coil current $I_2$.

* * * * *